(12) United States Patent
Basso et al.

(10) Patent No.: US 8,496,621 B2
(45) Date of Patent: Jul. 30, 2013

(54) PERISTALTIC MICROPUMP WITH EXCHANGEABLE PUMP HEAD

(75) Inventors: Nils Basso, Frankfurt am Main (DE); Christian Pommereau, Frankfurt am Main (DE); Alastair Clarke, Nantwich (GB); René Richter, Tharandt (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 12/415,232

(22) Filed: Mar. 31, 2009

(65) Prior Publication Data

US 2009/0292247 A1 Nov. 26, 2009

Related U.S. Application Data

(63) Continuation of application No. PCT/EP2007/008361, filed on Sep. 26, 2007.

(30) Foreign Application Priority Data

Oct. 7, 2006 (DE) .......................... 10 2006 047 613

(51) Int. Cl.
*A61M 1/00* (2006.01)

(52) U.S. Cl.
USPC .......................................................... 604/151

(58) Field of Classification Search
USPC ............. 604/151, 891.1, 519, 520, 31, 67, 604/71, 72, 122; 417/313, 474, 14, 53, 477.1, 417/477.2; 453/3
See application file for complete search history.

(56) References Cited

U.S. PATENT DOCUMENTS

| 5,462,525 | A | | 10/1995 | Srisathapat et al. |
| 5,558,639 | A | * | 9/1996 | Gangemi et al. ................ 604/67 |
| 5,582,593 | A | | 12/1996 | Hultman |
| 5,935,105 | A | | 8/1999 | Manning et al. |
| 2002/0169439 | A1 | * | 11/2002 | Flaherty ..................... 604/891.1 |
| 2002/0183693 | A1 | | 12/2002 | Peterson et al. |
| 2004/0191086 | A1 | | 9/2004 | Paukovits, Jr. et al. |
| 2005/0075624 | A1 | | 4/2005 | Miesel |

FOREIGN PATENT DOCUMENTS

| DE | 19745999 | 4/1999 |
| DE | 19916876 | 11/2000 |
| EP | 1045146 | 10/2000 |
| EP | 1535637 | 6/2005 |
| GB | 2012373 | 7/1979 |
| WO | 97/02059 | 1/1997 |
| WO | 2004/110526 | 12/2004 |
| WO | WO 2008/040478 | 4/2008 |

OTHER PUBLICATIONS

International Preliminary Report on Patentability dated Apr. 7, 2009, issued by the European Patent Office in International Patent Application No. PCT/EP2007/008361.

(Continued)

*Primary Examiner* — Nicholas Lucchesi
*Assistant Examiner* — Brooke Matney
(74) *Attorney, Agent, or Firm* — McDonnell Boehnen Hulbert & Berghoff LLP

(57) ABSTRACT

The present invention relates to a device for injecting a pharmaceutical into the human or animal body by means of a simply and quickly exchangeable motorized pump head.

34 Claims, 7 Drawing Sheets

OTHER PUBLICATIONS

International Search Report dated Jan. 21, 2008, issued by the European Patent Office in International Patent Application No. PCT/EP2007/008361.
Written Opinion dated Feb. 18, 2010, issued by the Singapore Patent Office in Singapore Patent Application No. 200901971-2.
Written Opinion dated Jun. 10, 2010, issued by the Singapore Patent Office in Singapore Patent Application No. 200901969-6.
9.0 Summary of Safety and Effectiveness, 510(k) Summary for Disetronic Multifuse™ Pump system, dated May 24, 1996, 4 pages.
AmerMed™ Multifuse Manual by Disetronic, 1996 AmerMed Corporation, v 1.01, 110 pages.
Declaration of Kurt Friedli dated Jun. 11, 2012.
Homecare Journal Feb. 1999.
Patient Information AmerMed Multifuse Infusion Pump, 1996 AmerMed Corporation, rev. Jan. 1997, 10 pages.
Disetronic, Disetronic Medical Systems AG, Invoice, Aug. 1997.
Dissertation of Markus Wiedmann, Munich 2001, 185 pages.

* cited by examiner

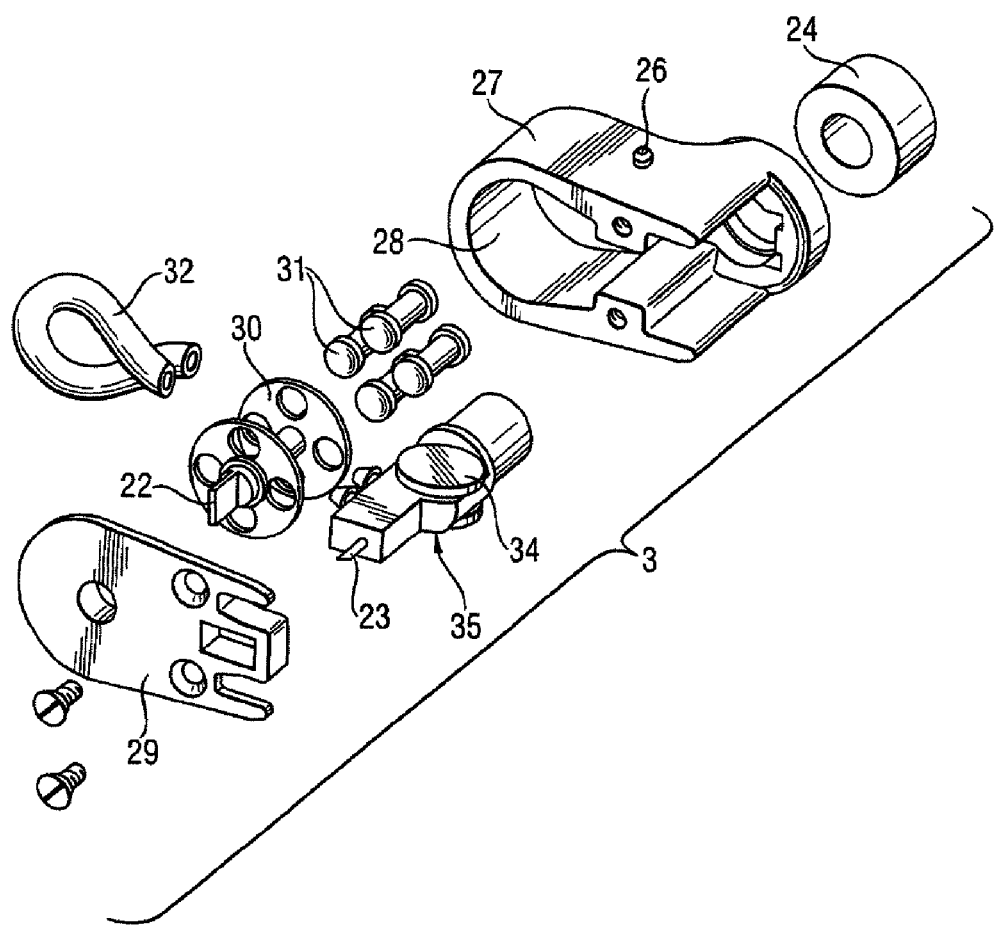

PERISTALTIC MICROPUMP WITH EXCHANGEABLE PUMP HEAD

The invention relates to a device for injecting a pharmaceutical into the human or animal body by means of a simply and quickly exchangeable motorized pump head.

Many pharmaceuticals must be injected into the body. This applies in particular to those which are inactivated or crucially lose activity on oral administration. These pharmaceuticals include in particular proteins (such as, for example, insulin, growth hormones, interferons), carbohydrates (e.g. heparin), antibodies or most vaccines. Syringes, medicament pens or medicament pumps are predominantly used for injection into the body.

The conventional insulin injection apparatus is the insulin syringe. This has been used since the start of insulin therapy, but has in recent years been displaced stepwise by introduction of the insulin pen, especially in Germany. Nevertheless, syringes are at present irreplaceable, e.g. if an insulin pen is lost or defective, and are used by many diabetics in combination with insulin pens. The freedom from maintenance and the universal availability is advantageous, especially during journeys.

Insulin syringes differ in their designation and graduation according to the concentration of the insulin to be used, U40 or U100. The insulin can be taken either from vials or else from the prefilled cartridges for insulin pens. This makes it possible to mix different types of insulin and reduces the number of injections necessary. Particular care about freedom from bubbles is necessary when the insulin is drawn into the syringe. The directly visible insulin dose which has been drawn in makes it possible for the user easily to check the amount of insulin injected. Nevertheless, skill and regular use are necessary for error-free administration with insulin syringes.

A further injection apparatus which is now very widely used around the world and especially in Europe is the insulin pen.

This medical apparatus which is the size of a marker pen was developed in the mid-1980s and is employed mainly for more intensive insulin therapy. A substantial innovation compared with insulin syringes is the use of an exchangeable medicament container. This container, also called carpule or cartridge, is filled with insulin when supplied by the manufacturer and is inserted into the insulin pen before use. When the pen is operated, a needle pierces the sealing disk of the cartridge and achieves parenteral injection of the preselected dose on administration of the insulin. An injection and release mechanism generates during the injection an injection stroke which advances a plunger or stopper in the cartridge and causes the preselected dose to be delivered into the target tissue. The mechanism usually consists of a rigid plunger stem with an overall length corresponding to the cartridge stopper stroke.

Insulin pens are divided into disposable and reusable ones. In the case of disposable ones, the cartridge and the metering mechanism form a unit prefabricated by the manufacturer and are disposed of together after the cartridge is emptied. Reuse of the metering mechanism is not intended. In contrast to prefilled pens, reusable pens make increased demands on the user. Thus, when the cartridge is changed, the plunger stem must be retracted into the starting position. This takes place, depending on the model, by twisting or sliding the plunger stem while simultaneously actuating a special function in the metering mechanism. This must be carried out very carefully by the user because malfunctions, e.g. sticking of the plunger stem, may occur occasionally owing to the daily use and the high mechanical stresses.

Reusable insulin pens are further divided into manual and semiautomatic pens. In the case of manual pens, the user exerts a force with the finger to actuate the injection button and thus determines the duration and progress of the injection. By contrast, with semiautomatic insulin pens, use is preceded by a manual tensioning of a spring which stores the necessary energy for injection. In the actual injection step, the spring is released by the user. The speed of injection is fixed by the power of the spring and cannot be adapted to personal needs.

DE 19 745 999 discloses a compact tubing pump of particularly small construction. This tubing pump is said to consist of a delivery head, a drive for the delivery head, a revolution rate controller and other components and accessories, the tubing pump being distinguished by the pump head being easily removable with the relevant drive from the housing and being replaceable by an identical, similar or different assembly.

A great disadvantage of this arrangement is that the pump head can be removed only together with the drive from the housing. This means that routine exchange of the pump head to maintain treatment which is as clean and aseptic as possible is costly, inconvenient and impractical.

Figure 1:
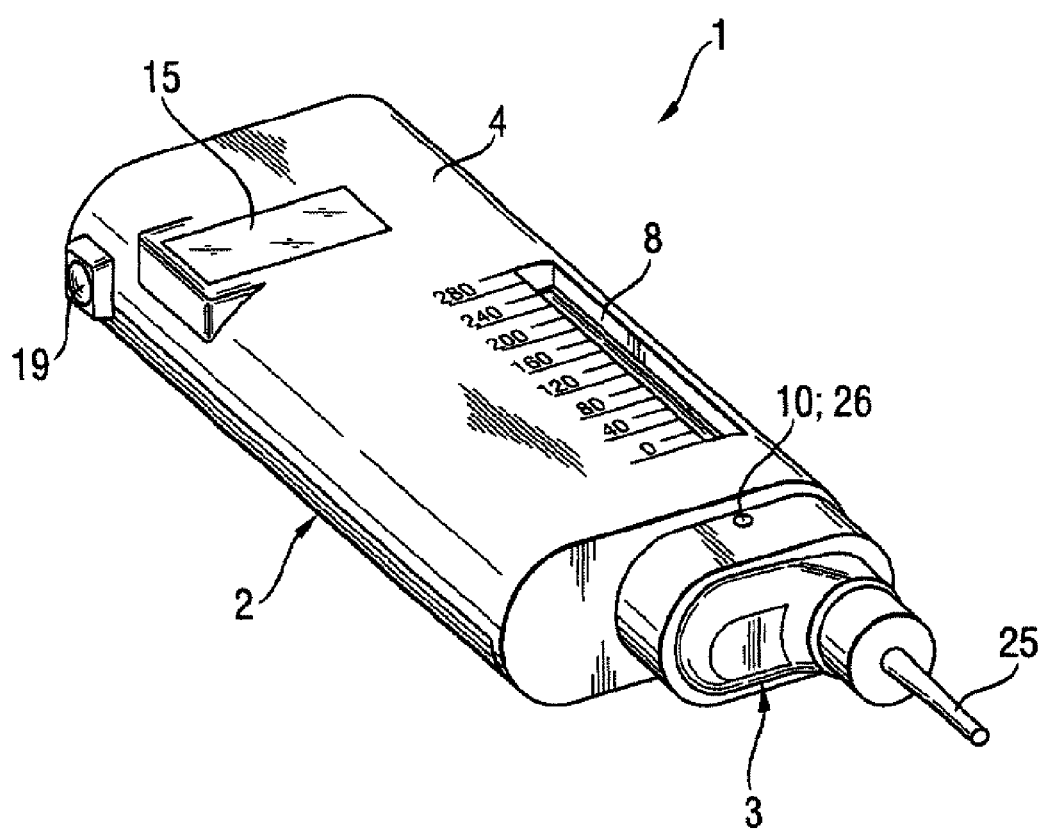
FIG. 1 shows a front view of the insulin pen.

The invention relates to a device for moving liquids which comprise a pharmaceutical in dissolved or suspended form, this device consisting inter alia of at least
  a) a motor;
  b) a reservoir;
  c) a pump head which is driven by the motor from a) and by means of which the liquid is conveyed out of the reservoir;
  d) control electronics;
  wherein the pump head is equipped with detachable and reconnectable interfaces to the motor from a) and/or to the reservoir from b) and/or to the control electronics from d).

A device consists of one or more components connected together and serves a particular purpose. The purpose may be fixed by a particular type of use. One purpose is for example the use for injecting a pharmaceutical, in particular injecting insulin into the human or animal body.

The interface between the pump head and the motor functionally connects the two parts. This functional connection involves the movement of the motor being converted into pumping work. The motor can for this purpose be supplied with energy in various ways. Preference is given in this connection to operation by means of a battery (for single use or rechargeable) or by means of domestic current, possibly through an interposed adapter to adjust the voltage and/or by means of solar cells. The pumping work serves to convey liquid out of the reservoir. For this purpose there is an interface between the pump head and the reservoir. This interface is designed so that the movement of liquid to convey the liquid out of the reservoir can be started, maintained and stopped by appropriate operation or control of the motor and/or pump head. Tubings are included in these interfaces. The connections should be designed to be fluid-tight. There is a further interface between pump head and control electronics. This interface serves to transmit sensor data, e.g. from a flow sensor, temperature sensor, "glucose sensor" or other sensors, to the control electronics. The interface may have an electrical, optical, wireless configuration. The control electronics can be used to maintain the operational state of the apparatus, the coordination of the various constituents, the exchange and processing of operating data between the various components, the exchange of information and input relating to the user or monitoring of normal operating functions and of safety in relation to the user.

The interfaces of the pump head to the motor, to the reservoir and to the control electronics are distinguished by being easily and quickly releasable and reconnectable. The qualification for easy release and connection relates to an average operator of the device who has previously read a description which may have been included. Simple release of the interfaces can be effected for example by disengaging the parts, by pressing and subsequently rotating the parts, by shifting a lever, sliding a slide button, or pressing a pushbutton to release from a locking mechanism, and also by unscrewing, decoupling or the like. Simple connection of the interfaces can take place for example by pushing, sliding, twist engagement, screwing on, coupling on, clicking on, shifting a lever or the like. Simple release and connection of an interface exists in particular when release and connection takes place not with the aid of a tool but solely by employing the physical strength of a person (e.g. a patient, member of the medical staff), in particular resulting from the movements of the arms, hands and/or fingers.

The invention consists in a preferred embodiment of a device as described above, in which the pump head is exchanged after operation (i.e. actuation of the device) for another pump head.

The pump head is replaced in particular every time, or else every second, third, fourth, fifth, sixth, seventh, eighth, ninth, tenth time or at longer intervals in each case after use of the device in a cycle of "switching on, maintaining and switching off" the pump head for operation. The pump head is changed whenever the pumping capacity declines. Especially in cases of use where value is placed on cleanliness and/or the minimum number of microbiological organisms (for example in medical treatments), the pump head should be changed frequently, i.e. every time or every second time after use.

The invention consists in a further preferred embodiment of a device as described above, in which the pump head carries a needle. A needle means an injection needle for medical use. A needle includes a cannula (usually made of metal) through which liquid or gas can be injected or aspirated into/out of the human or animal body, and a holding device which is attached on top of the cannula and by means of which the needle can be affixed to a syringe, a catheter, a medical pump, a medicament pen (e.g. insulin pen) or another medical apparatus. The needle carried by the pump head serves in particular for injecting the liquid derived from the reservoir (e.g. insulin preparation) into the human or animal body.

The invention consists in a further preferred embodiment of a device as described above, in which the motor consists of a micromotor. A micromotor is distinguished by small dimensions. Its length is between 3 and 0.5 cm, its width is between 0.5 and 1.5 cm and its height is between 0.5 and 1.5 cm. A micromotor for use in the device according to the invention is based in particular on an electromagnetic drive.

The invention consists in a further preferred embodiment of a device as described above, in which the reservoir consists of a commercially available cartridge for receiving a medicament. Such cartridges are available for various pharmaceuticals. Known cartridges (also called vial) are those comprising insulin of varying type (e.g. slow-acting such as Lantus or fast-acting such as Apidra or normal-acting such as Insuman) or amount (e.g. 100 I.U., 200 I.U., 300 I.U., 500 I.U., 1000 I.U. or another amount) as solution or suspension and as mixture of different insulins. Insulin cartridges (insulin vial) are used for injecting insulin, by means of syringes and insulin pens, into the human body or for continuously supplying, by means of insulin pumps, the insulin to the human body. A manufacturer of such insulin cartridges is Sanofi-Aventis in particular. Commercial supply of insulin cartridges usually takes place via pharmacies in most countries.

The invention consists in a further preferred embodiment of a device as described above, in which the liquid comprises insulin. The insulin present may be of varying type (e.g. slow-acting such as Lantus or fast-acting such as Apidra or normal-acting such as Insuman) or amount (e.g. 100 I.U., 200 I.U., 300 I.U., 500 I.U., 1000 I.U. or another amount) as solution or suspension and as mixture of different insulins. The insulin may be of animal origin or be produced by genetic manipulation.

The invention relates to the use of a device in one or more of the embodiments as described above for injecting a substance into the human or animal body. Such a substance is in particular insulin in solution or as suspension. An injection in this connection is to be distinguished in particular from supply through a pump. On injection, the substance is introduced to the body within a short time (e.g. 5 to 60 seconds) by means of a syringe or a medicament pen (e.g. insulin pen), usually as previously fixed total volume. The medicament pen comes into contact with the body only during the direct injection. A substance is supplied by a medicament pump over a longer period (from 60 sec. up to several hours), and the medicament pump is usually attached to the body.

The invention further relates to the production of a device in one or more of the embodiments as described above, where
 a) a motor is provided;
 b) a reservoir is provided;
 c) a pump head is provided;
 d) the individual constituents according to a) to c) are assembled to give a functional unit.

The assembly of the device according to the invention to give a functional unit means the production of a device according to the invention in a state ready for operation. The functional unit of the device according to the invention is able after operation starts in particular to remove liquid from the reservoir through the action of the motor-driven pump head. This removed liquid can, in a further possible use of the functional unit, be injected by the latter into a human or animal body.

The invention also relates to a medical apparatus for injecting a pharmaceutical into the human or animal body, comprising inter alia
 a) a housing and/or
 b) an adjusting mechanism for presetting an amount of the pharmaceutical to be delivered by the medical apparatus, and/or
 c) a display and/or
 d) a release mechanism for starting up and carrying out the injection;
 which additionally comprises at least one device according to the invention in one or more of the embodiments as described above.

A medical apparatus for injecting a pharmaceutical is in particular a pen. Pens are known in particular for injecting insulin (insulin pen). Insulin pens are available in pharmacies. Examples of insulin pens currently on the market are the Opticlick, Optipen Pro, Optiset and insulin pens of other manufacturers.

A housing is the outer cover of such a medical apparatus, which may include a protective cap, depending on the design. The housing may be made of plastic or metal. It usually has an elongate shape, usually comprises recesses, orifices or windows, includes an inner cavity and is suitable for receiving and positioning further components.

An adjusting mechanism makes it possible to preset an amount of a pharmaceutical which is to be injected later. The adjusting mechanism can be operated mechanically or electronically. The adjusting mechanism is designed so that the preset amount of the pharmaceutical can be corrected until the actual injection is carried out.

The display serves to represent the preset amount of the pharmaceutical which is to be injected. The display can take place in the mechanical way or in the form of an LCD display. The release mechanism includes any removal of air bubbles which is necessary before carrying out the actual injection, and the starting of the injection process up to completion of the injection by appropriate actuation of the motor and/or of the pump head. The medical apparatus according to the invention may comprise a second display or further displays.

The first or the second or a further display may be used to represent the current status of the apparatus during the injection, e.g. residual amount remaining, temperature, glucose level etc. Such a display may for example represent the progress of the injection by means of a progress bar.

A medical apparatus as described above includes in a preferred embodiment at least one means for storing and/or processing data and/or signals, and at least one interface for transferring data and/or signals to and/or from an external technical unit (consisting for example of a PC on which a program for storing and/or processing data and/or signals is installed, which is configured to store and/or process data and/or signals.

A medical apparatus as described above exists in particular for injecting insulin, or GLP-1 or a heparin such as, for example, Lovenox. The insulin may be a long-acting, a short-acting, a mixed insulin or a normally-acting insulin of animal or human origin or one which has been produced conventionally or by genetic manipulation, and may be in the form of a solution or suspension.

The medical apparatus according to the invention in one or more of its embodiments can be used for the prophylaxis and/or therapy of a disease and/or dysfunction of the body by means of a substance whose pharmacological activity is diminished or lost in the gastrointestinal tract.

The medical apparatus according to the invention in one or more of its embodiments can be used in particular for the treatment of diabetes, e.g. by administration of GLP-1.

The medical apparatus according to the invention in one or more of its embodiments can additionally be used for administering a peptide hormone (e.g. glucagon, thyroxine, pituitary hormone, hypothalamus hormone, leptin inter alia) or a growth hormone (e.g. human growth hormone).

The medical apparatus according to the invention in one or more of its embodiments may further be used to administer a heparin (e.g. low molecular weight heparin) and/or Lovenox.

Finally, the medical apparatus according to the invention in one or more of its embodiments can be used to administer a vaccine (e.g. live or dead vaccine; vaccine for the treatment of influenza, measles, mumps, poliomyelitis, rabies, tetanus, whooping cough, immunodeficiency diseases inter alia) and/or for administering antibodies (e.g. monoclonal or polyclonal antibodies for treating a bacterial or viral infection, dysfunction of the immune system, allergy, cancer inter alia).

The invention further relates to the production of a medical apparatus for injecting a pharmaceutical into the human or animal body, where
 a) a housing is provided;
 b) an adjusting mechanism is provided to preset an amount of a pharmaceutical which is to be delivered by the medical apparatus;
 c) a display is provided;
 d) a release mechanism is provided;
 e) possibly electronic constituents are provided;
 f) at least one device according to the invention in one or more of the embodiments as described above is provided;
 g) the individual constituents from a) to f) are assembled to give a functional unit.

A device consists of one or more components and serves a particular medical purpose, in particular injection of a substance into the human or animal body. One component consists of one or more elements and serves to comply with a technical or non-technical function. A function is technical if it relates to a transfer of force, work, energy, material (substance), data and/or signals, the maintenance of the structure and/or form or the storage of a substance, or storage of information. A function is not technical if it relates to the input or output of information by or to the user of the device or of a substance by or to the user of the device.

A component may be for example part of a technical apparatus which provides a partial function in relation to the overall function of the apparatus.

A component is for example a reservoir. Reservoir may be an exchangeable cartridge comprising a substance (in particular a medicament such as, for example, insulin). The exchangeable cartridge may be suitable in particular for use in an insulin pen or another device for injecting a medicament into the human or animal body. Another example of a technical component is a device for pumping or a pump. Further examples of technical components are in particular syringes, needles, plunger stems, metering units, mechanical displays, tubings, seals, batteries, motors, transmissions, electronic displays, electronic memories or electronic controls. The meaning of purpose in connection with the technical device is intended to be in particular the movement of liquid from one place to another. One purpose is for example defined by moving a liquid volume from a reservoir to an outflow line. The purpose may also be injection of a medicament into the human or animal body.

A component may be connected in a technical manner to one or more other components in order to comply with a purpose together. A technical connection is for example a connection of components which is suitable for transmitting force, work, energy, material (substance), data and/or signals. The components can be connected for example via a mechanical coupling, a fixed mechanical connection (gluing, screwing, riveting, via linkage or the like), a toothed wheel, a latch, an interlock means, a metallic wire, an optical waveguide, a radio link, an electromagnetic field, a light beam or the like.

Injection is the introduction of substances, in particular of liquids, by means of a cannula together with syringe or functionally comparable device such as in particular a pen into the human or animal body. Inter alia, subcutaneous, intramuscular, intravenous, intracutaneous and intraarticular injection is known. Subcutaneous injection takes place underneath the skin and is relatively easy to carry out, not very painful and can be undertaken by the patient himself. Intramuscular injection takes place into a muscle. Since greater risks exist in this case, such as, for example, painful periosteal injury, this is usually undertaken by medical staff. Intravenous injection takes place following venepuncture directly through a vein.

In intracutaneous injection, a pharmaceutical is passed directly under the dermis. In intraarticular injection, a liquid is injected into a joint. Injection of a substance into the human or animal body is to be distinguished in particular from introduction of a substance through a medicament pump, an infusion or another type of continuous supply taking place over a certain time.

A cannula is essentially a hollow needle which is usually made of metal (e.g. steel, stainless steel, gold, silver, platinum). The end of the cannula is frequently sharpened by grinding at an angle. The cannula may be pointed and/or sharpened at one end and blunt at the other end, but it may also be pointed and/or sharpened at both ends. The cannula has at one of the two ends a usually conical attachment made of, for example, plastic by means of which the hollow needle can be arranged for example by pushing or screwing onto a medical apparatus such as, for example, a syringe, a medicament pen, in particular an insulin pen, a medicament container or a medicament pump. The cannula serves, in functional interaction with a syringe, a pen, a pump or another medical apparatus suitable for the purpose, to remove or supply a liquid from or into the human or animal body.

The diameter of the cannula (external diameter) is usually stated in mm or in gauge (18 gauge=1.2 mm; 20 gauge=0.9 mm; 21 gauge=0.8 mm; 22 gauge=0.7 mm; 23 gauge=0.6 mm; 25 gauge=0.5 mm; 27 gauge=0.4 mm). Another parameter for characterizing the cannula is its length. Typical lengths of cannulas are 40 mm, 30 mm, 25 mm, 8 mm, 6 mm and other lengths.

A medical apparatus is in particular an apparatus for injecting the substance into the human or animal body. Besides a syringe, it is possible for such an apparatus for injection to be a medicament pen such as, for example, an insulin pen. Medicament pens are suitable in various form and for various purposes and are obtainable on the market from various manufacturers (e.g. Optiklick, Optipen, Optiset).

Every insulin pen must satisfy numerous requirements in relation to ease of operation in order to make safe and fault-free use possible. The basic requirement is the display of the preselected dose and of the amount remaining in the cartridge. The setting of the dose, and completion of the injection process should moreover be made audible, perceptible by touch and visible. This safety requirement arises in particular from the limited perception capacities of elderly type 2 diabetes patients.

Besides insulin pens with needles, also employed for insulin therapy are needle-free injection systems. A current example of the use of needle-free injection system is the Injex injection system of Rösch AG. With this injector, extremely high pressure is used to shoot the insulin through a microneedle into the adipose layer of the skin. An elastic spring which is tensioned manually before injection stores the necessary injection energy therefor. The injected material is in this case distributed homogeneously and conically in the adipose tissue.

A non-negligible advantage of this apparatus is the needle-free injection of the medicament, which in some patients reduces the psychological inhibition threshold for insulin administration. In addition, needle-free injection precludes infection of the puncture site. Disadvantages compared with conventional insulin pens proved to be the transfer of the insulin into special cartridges, the comparatively larger mass of the apparatus, and the inclusion of further accessories for tensioning the spring.

Insulin pumps differ from insulin syringes by being completely automatic infusion systems for continuous subcutaneous injection of insulin. They have approximately the size of a cigarette pack and are worn permanently on the body. Short-acting insulin is injected through a catheter and a needle located in the skin into the cutaneous tissue according to the program preset by the patient. The task of the insulin pump is to imitate the continuous output of insulin by the pancreas to reduce the blood glucose level, but without being able to regulate the blood glucose with closed-loop control. Because of the continuous and adaptable supply of insulin, these pumps have advantages in particular for people engaged in sporting activities and whose daily routine varies greatly. It is possible with insulin pump therapy to compensate for large variations in blood glucose, e.g. in diabetics with a pronounced DAWN phenomenon, which can be controlled with conventional methods only with increased effort. One disadvantage is that when the insulin supply is interrupted owing to the lack of an insulin reservoir in the human body, severe metabolic derangement may occur. Insulin pumps are available in various technical configurations, and apparatuses with syringe-like containers have become established during the technical development. In analogy to the insulin pens with needles, the insulin is present in a reservoir with moveable stopper. The latter is moved by a motor-driven plunger stem.

Owing to the completely automatic and continuous delivery of insulin, the pumps are provided with a large number of security systems in order to protect the user from malfunctions with serious consequences. However, this does not mean that responsible and anticipatory use of the apparatus is unnecessary.

On the basis of the current injection apparatuses and further technological development in medical and microsystems technology there is an evident trend to completely automatic miniaturized medicament metering systems. Further development might go in the direction of implantable and extracorporeal medicament metering systems. The aim of implantable insulin pumps is to free the diabetic from the daily injection of insulin without the need to wear an external apparatus on the body.

Insulin pens are concentrate in the essential ergonomic and safety features in the EN ISO standard 11608. This likewise includes the geometric/material properties of the insulin cartridges and pen needles. The handling and the operation of a pen is thus substantially uniform and independent of the model for the user.

The contents of the EN ISO standard 11608 where this relates to insulin pens, insulin cartridges and needles is hereby expressly incorporated in the present disclosure by reference.

In the design of the pens there are some considerable differences to be found in the pens of the various manufacturers. The reasons therefor are for example the designation for different target groups (children, elderly people). Because of the requirements of the EN ISO standard 11608, the differences are confined in particular to the injection mechanism and the release mechanism. The dose selector and the dose display are mostly subject to ergonomic requirements and result from the general design conditions of the respective model.

The essential functional element of an insulin pen is the injection mechanism. It determines the type and size of the pen and the design of the release mechanism and of the dose selector. The mechanism translates the dose preset on the dose selector with the injection energy derived from the release mechanism into an injection stroke of the stopper in the cartridge. This energy is transmitted either directly to the injection mechanism or through a motion-modifying transmission.

It is technically possible for the injection mechanism in the shape of the plunger stem to vary in form.

In the insulin pens currently available on the market, solutions with a rigid (e.g. threaded spindle, toothed rack) or a flexible (e.g. curved toothed rack, curved compression spring) design have become established. Other possible configurations such as telescopic plunger stem (e.g. screw mechanism, belt and chain drive, hydraulic transmission, coupled transmission) are not employed in the insulin pens currently commercially available.

The design solutions of the rigid and flexible type vary widely and depend on the kind of pen, i.e. reusable pen or prefilled pen. Plunger stems employed are threaded spindles or toothed racks or combinations of the two. In the dose selector, an angle of rotation corresponding to the dose is preset with the aid of detent devices and is transmitted by subsequent screw mechanisms and toothed gears to the injection mechanism and transformed into the injection stroke.

Delivery of the medicament takes place by specifying an injection stroke and the resulting displacement of the stopper. The amount of liquid delivered depends on the injection stroke and the internal diameter of the cartridge. To avoid dosage errors, air bubbles must be completely removed in accordance with manufacturers' specifications and the EN ISO standard 11608. In addition, after delivery of the liquid, a sufficiently long time should be allowed to elapse in order to ensure a steady state, i.e. normal pressure of the liquid and relaxation of the stopper in the cartridge.

The reservoir for the medicament (also referred to as cartridge) influences the construction and functional structure of the medicament pen. Partial functions which can be distinguished in this connection are firstly a protective function for the medicament, then a conveying function and finally a coupling function to the injection system of the medicament pen. The protective function is achieved by the cartridge as a whole, i.e. by stopper, glass body and sealing disk. The conveying function for the medicament is conferred by the stopper, which is displaced with the aid of the injection mechanism and brings about a change in volume in the cartridge. The coupling function to the injection system finally is produced by sealing means (e.g. sealing disk). In an automatic medicament pen (e.g. automatic insulin pen), the injection energy is applied by a drive with subsequent transmission. An energy supply and control unit are additionally necessary.

In the injection mechanism according to the invention, the medicament (e.g. through insulin) is conveyed not by displacement of the stopper by means of an injection mechanism, but by introducing a pump device. The pump device is inserted between cartridge and injection system and is to be provided with appropriate interfaces.

The pump device can be provided with a flow sensor. It is in direct contact with the medicament, e.g. insulin, thus giving rise to additional requirements such as reduced organism count, sterility, biscompatibility inter alia.

On application of this functional principle, numerous variables (e.g. the liquid pressure in the medicament container) are altered by comparison with a conventional medicament pen for injection (e.g. an insulin pen), because a sub-atmospheric pressure arises when the medicament is sucked out.

Insulin cartridges serve as primary packaging for the medicament and must satisfy high standards. This relates to the dimensional accuracy of the cartridge in relation to the accuracy of dosage and compatibility with other components. The EN ISO standard 11608-3 is concerned with these requirements and describes the fundamental aspects and the geometrical/material construction without unnecessarily restricting the shape of the cartridge. The pharmaceutical impermeability of the cartridge must likewise be ensured.

The cartridges consist of a plurality of subcomponents. The principal one is the cylinder of pharmaceutical glass with high neutrality and chemical resistance to insulin. Before filling, the surface quality of the cylinder is improved by siliconization. This surface treatment reduces the sliding and breakaway forces of the stopper, increases the accuracy of dosage and reduces the dissolving out of glass constituents during a long storage time. The degree of siliconization correlates in this connection with the level of the frictional forces of the stopper, a limit being set by the sensitivity of the insulin to the silicone.

The cartridge is sealed at both ends by elastomeric closure parts, the stopper and the sealing disk. Crucial points in this connection are the demonstrated mechanical impermeability in various pressure situations, and the microbiological impermeability to all organisms in long-term tests. Further important points are the maximum allowable stopper forces and the number of punctures of the sealing disk with a cannula.

Pen needles are sterile disposable products employed to guide the insulin out of the cartridge into the target tissue. They are subject, just like cartridges, to strict requirements because the real functionality of the insulin pen is achieved only through cooperation of the two components. The needle consists of a cannula which is ground at both ends and which is set in a cartridge attachment piece. Optimized grinding of cannulas makes it possible for insertion into the target tissue to be substantially painless for the patient and causes only slight tissue damage on withdrawal again. Likewise, the cartridge sealing disk is pierced without extensive fragmentation. This is an obligatory requirement because the impermeability of the cartridge must be ensured also when the needle is regularly changed. The cartridge attachment piece ensures a firm fit on the insulin pen.

Even if pen needles show signs of wear which are scarcely visible to the eye after being used two or more times, they should nevertheless be changed after each injection for reasons of sterility. In addition, crystallized insulin may block the needle. Moreover, air gets into the cartridge if there are temperature variations, equally causing dosage errors. Thus, a temperature change of only 15 K causes up to 15 µl of air to enter the cartridge.

Microfluidics is a subsection of microsystems technology and includes the design, production, use and investigation of microsystems which manipulate and treat amounts of fluid in channel cross sections with dimensions of from 1 µm to 1 mm. Microfluidic systems are employed in medical technology, biochemistry, chemical engineering and analysis, and microreaction technology. These microsystems may have dimensions in the millimeter and centimeter range because it is the amount of fluid and not the size of the microfluidic system which is important for practical use. In addition, such systems show significant differences from conventional fluidic systems because of the small amounts of fluid and often small system sizes. Miniaturization is accompanied by a change in the behavior of the fluid flow because surface-linked effects and electrostatic and electrokinetic forces dominate. New approaches are therefore necessary for the design, production and characterization of microfluidic components, e.g. micropumps and sensors. The constant energy density of the actuators results in their output falling, so that they are not comparable with conventional components in the macro sector. For this reason, external actuators are frequently employed and at times considerably increase the dimensions of the overall system. In addition, the physics and chemistry of the particles and molecules to be transported limit the miniaturization of microfluidic components.

Diabetes mellitus is a disorder in which the body is itself unable to produce and appropriately use any, or sufficient, amounts of insulin. Insulin is required to transport glucose from the blood into the cells of the body. The blood glucose level is continuously kept constant within narrow limits (60-100 mg % or 3.33-5.55 mmol/l). This takes place through the interplay of the two hormones insulin and glucagon.

Diabetes mellitus is diagnosed after taking blood by means of appropriate laboratory apparatuses. An elevated blood glucose level must be detected on at least two different occasions in order to confirm the diagnosis.

Diabetes mellitus is the term used when the glucose level measured in the blood plasma exceeds the stated value in at least one of the indicated cases:
a) fasting blood glucose—7.0 mmol/l or 126 mg/dl
b) blood glucose two hours after a dose of 75 mg of glucose (oral glucose tolerance test)—11.1 mmol/l or 200 mg/dl
c) blood glucose 11.1 mmol/l or 200 mg/dl associated with severe thirst (polydipsia), frequent urination (polyuria) or loss of weight.

Untreated diabetes leads to elevated blood glucose levels which may lead to various symptoms and late consequences such as, for example, polyneuropathy, microangiopathy, macroangiopathy, retinopathy, nephropathy and others. The risk of late damage from diabetes is less when the nonenzymatic glycation of erythrocytes (HbA1c level) is lower.

Diabetic coma is a life-threatening acute complication of diabetes. The blood glucose level may in such cases extend above 1000 mg/dl, associated with excessive acidity in the blood (metabolic acidosis). Diabetic coma can be induced inter alia by infections, intake of too much carbohydrate, alcohol abuse or incorrect insulin dosage.

A distinction is made between type 1 diabetes and type 2 diabetes. In type 1 diabetes there is an absolute insulin deficiency from the outset and treatment is possible only with insulin dosage.

Type 2 diabetes is characterized by a reduced insulin sensitivity and a relative insulin deficiency. Type 2 diabetes can usually be treated initially with diatetic measures and tablets. Insulin replacement frequently becomes necessary during the course of the disorder.

Type 2 diabetes has become a widespread disease predominantly in industrialized countries. Overeating, lack of exercise and obesity are regarded as the main cause. Type 2 diabetes can be effectively counteracted by exercise training and diabetic measures, especially aiming at weight reduction. It is also possible in the case of type 2 diabetes to employ oral antidiabetics such as, for example, acarbose, biguanides, sulfonylurea, glitazone and others. Therapy using insulin is necessary when the blood glucose level can no longer be kept in or near the normal range with sufficient permanence by means of said measures.

Various insulins are available for insulin therapy. A distinction is usually made according to the duration of action or chemical structure. An analog insulin has different amino acids at individual positions compared with human insulin. The properties may be changed thereby.

The rapid-acting insulins include human insulin and various rapid- and short-acting insulin analogs such as glulisin (proprietary name: Apidra), lispro (proprietary name: Humalog) and aspart (proprietary name: Novo Rapid).

Slow-acting or extended-acting insulins are NPH insulin (human insulin with an action extended by neutral protamine hagedorn), zinc insulins and various insulin analogs such as glargine (proprietary name: Lantus) and detemir (proprietary name: Levemir).

Also used in insulin therapy are mixed insulins and, recently, inhaled insulins. Mixed insulins consist of a rapid-acting insulin and an extended-acting insulin in various mixing ratios. 10/90%, 25/75%, 30/70%, 50/50% mixtures are usual. Insulin therapy must always be accompanied by regular determinations of the blood glucose level.

In conventional insulin therapy, a defined amount of mixed insulin is injected at fixed times. More intensive conventional insulin therapy is employed predominantly for the therapy of type 1 diabetics. In this case, a basic supply is ensured with an extended-action insulin (basal) and a rapid-acting insulin (bolus) is given additionally at meal times.

Continuous subcutaneous infusion of insulin by means of a pump is suitable namely for type 1 diabetics. The insulin is not injected but is passed into the body by a small pump. The pump is permanently present on the body. The insulin is supplied through a catheter with cannula. The insulin pump usually delivers rapid-acting insulin at small equal intervals over a prolonged period.

Glucagon-like peptide 1 (GLP1) is, alongside glucose-dependent insulinotropic peptide (GIP), one of the most important representatives of the incretins. Incretins are produced as hormones in the intestine and regulate inter alia the blood glucose level by stimulating insulin release in the pancreas.

The amount of intestinal hormones produced depends on the amount of carbohydrates taken in orally. The GLP1 level increases much more after oral glucose intake than after intravenous administration of glucose. It has been possible to show by investigations that intravenous infusion and subcutaneous injection of GLP1 in type 2 diabetics leads in many cases to complete normalization of the blood glucose level. A problem is that GLP1 is inhibited within a very short time by dipeptidylpeptidase IV (DPP-IV). Subcutaneous injection of GLP1 can maintain effective plasma concentrations over only about 1-2 hours. A solution in the direction of a persistent effect of GLP1 might be discoverable in the development of longer-acting GLP analogs or else inhibition of DPP-IV by pharmaceuticals.

Growth hormones are substances which stimulate growth in humans, animals and plants. Known examples are somatotropin (human), bovine somatotropin (cattle) and auxin, gibberellic acid (plant).

Somatotropin (STH) is also known under the names human growth hormone (HGH) and growth hormone (GH). STH is a peptide hormone with 191 amino acids. Production takes place in the anterior pituitary under the control of somatotropin-releasing factor (SRF; GHRH; GRF) from the hypothalamus. STH is absolutely necessary for normal linear growth. Reduced production or reduced response of the cells to STH results in short stature. Overproduction results in gigantism or acromegaly.

Short stature caused by growth hormone deficiency has been treated for some years by administration of STH. It was initially obtained from cadaver pituitaries before it became possible to produce STH by genetic manipulation in 1985.

Interferons are produced as tissue hormones by human or animal leucocytes, fibroblasts or T lymphocytes. An interferon is a protein or glycoprotein with an immunostimulating (e.g. antiviral) or antihormonal effect. Interferons are divided into alpha-interferons, beta-interferons and gamma-interferons. Interferons are obtainable from various manufacturers for indications such as viral diseases (e.g. SARS), cancer, multiple sclerosis, hepatitis B/C, hepatitis C.

A vaccine is a composition produced biologically or by genetic manipulation and comprising inter alia individual proteins and/or RNA or DNA fragments and/or killed or attenuated pathogens (e.g. influenza, SARS, poxvirus, pathogens of measles, mumps, rubella, poliomyelitis, pathogens of whooping cough).

Known types are live vaccines (e.g. cow pox), attenuated live vaccines with attenuated viruses or bacteria (e.g. MMR vaccine, yellow fever, poliomyelitis) and dead vaccines with inactivated or killed viruses or bacteria or constituents thereof (e.g. influenza, cholera, bubonic plague, hepatitis A).

Heparins are substances employed therapeutically to inhibit blood coagulation. Heparins consist of in each case alternating sequences of D-glucosamine and D-glucuronic acid or L-iduronic acid. Chain lengths consisting of 5 units may be sufficient for anticoagulation.

The polysaccharide chains mostly have a molecular weight of between 4000 and 40 000. Besides unfractionated heparins, use is also made of low molecular weight fractionated heparins with a molecular weight of about 5000. Heparins are not absorbed from the gastrointestinal tract but must be administered parenterally. Heparins act by binding to antithrombin III and thus accelerating the inactivation of activated coagulation factors.

Lovenox (also known as clexane) is a commercially available pharmaceutical preparation with the pharmacologically active ingredient enoxaprin sodium. The active ingredient is one of the low molecular weight heparins with a linear dose-response relation and a constantly high bioavailability.

Areas of indication for Lovenox are the primary prophylaxis of deep vein thromboses, therapy of deep vein thromboses with or without pulmonary embolism, therapy of unstable angina pectoris and of the so-called non-Q-wave myocardial infarction, and thrombosis prophylaxis and anticoagulation during hemodialysis.

EXAMPLES

Figure 2:
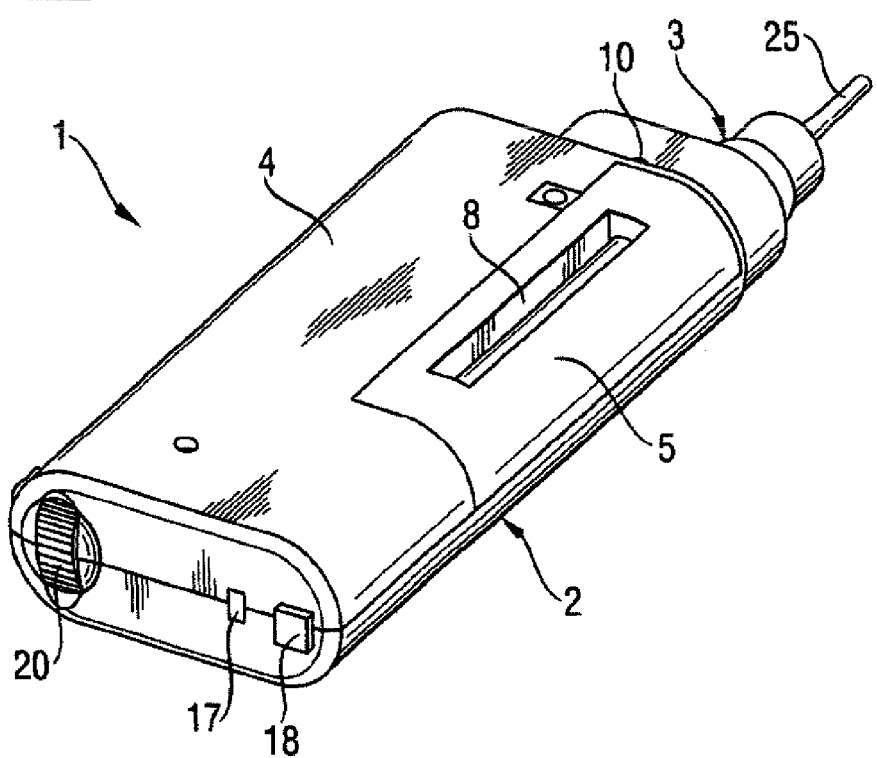
FIG. 2 shows a rear view of the insulin pen.
Figure 3:
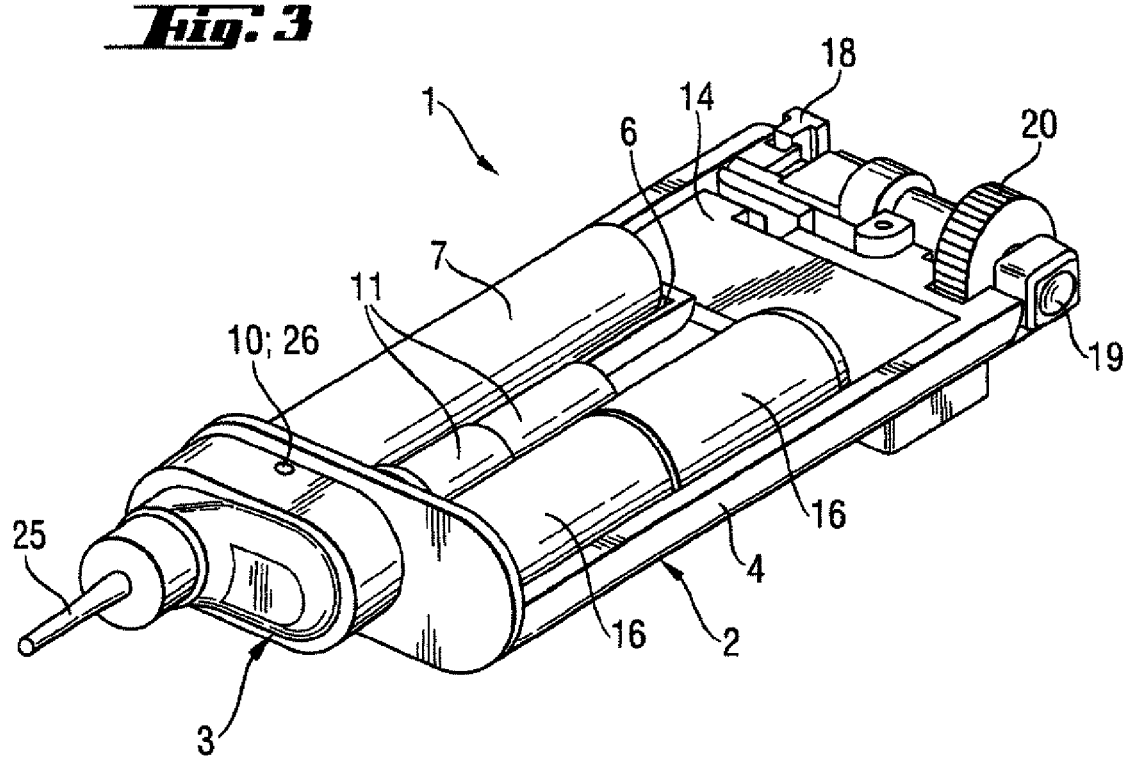
FIG. 3 shows individual components of the insulin pen.
Figure 4:
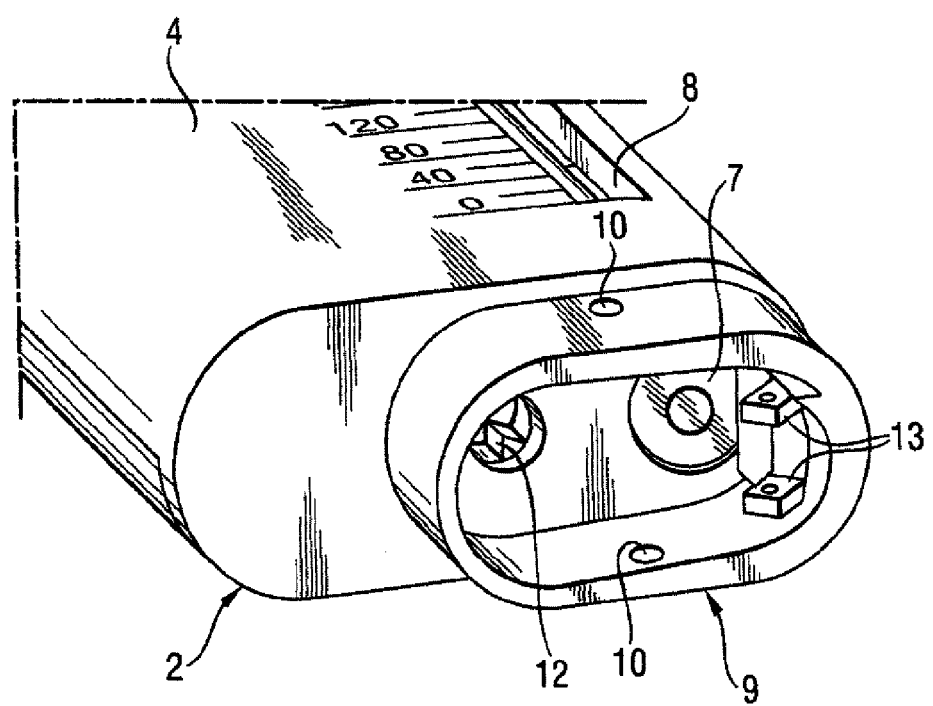
FIG. 4 shows the interface to the pump head.

The insulin pen consists of a main apparatus with exchangeable pump head. The main apparatus is reusable. It consists of a housing in which pump drive, sensors, electronics and energy supply are accommodated (FIG. 1; FIG. 2; FIG. 3). It is further provided with interfaces to external apparatuses, and with a start button and metering button. The pump head is a disposable part and is employed only over a short period (1-3 days). It has interfaces with the main apparatus and with the pen needle (FIG. 4).

Exchangeable Pump Head

Figure 5A:
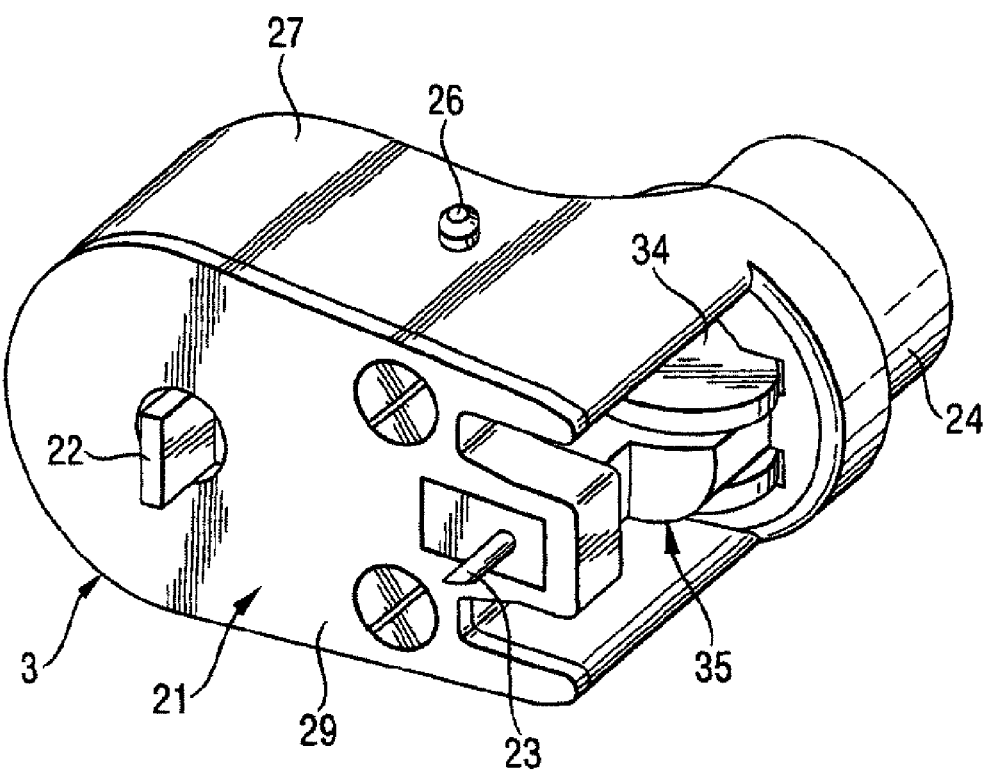
FIG. 5 shows the exchangeable pump head.

The pump head consists of a pump chamber (tubing pump) and a flow sensor (impeller meter) which are accommodated in a housing. The housing has interfaces which can easily be separated and closed again (FIG. 5).

Figure 6:
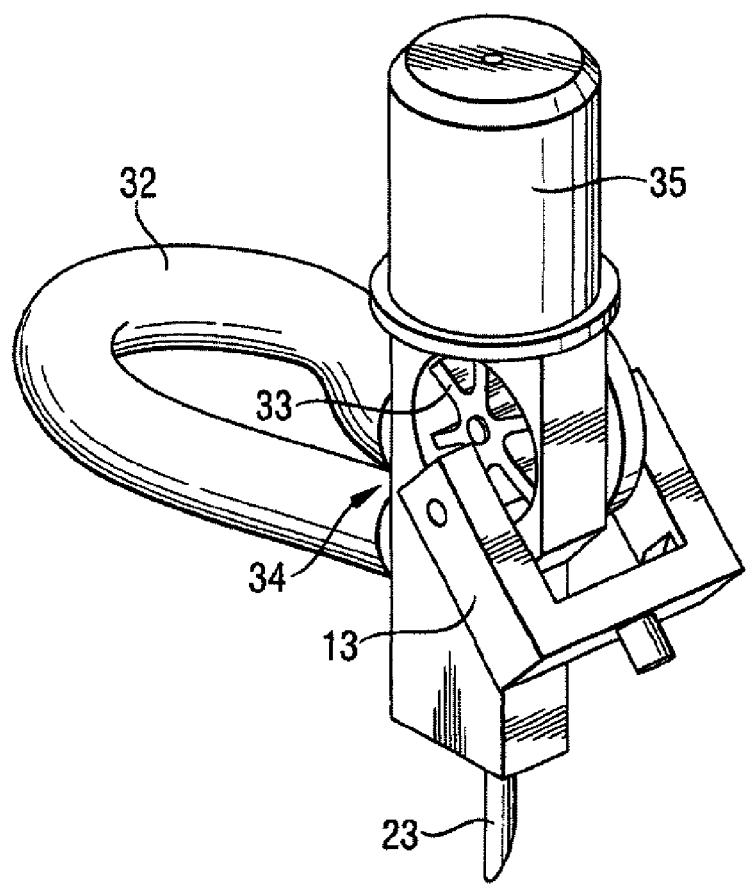
FIG. 6 shows the impeller with interrupter.

The flow sensor in this embodiment is separated into two components. In the pump head there is an impeller which can be produced at reasonable cost (test object). This is changed together with the pump head. The rotation of the wheel is detected with a slotted interrupter which is firmly integrated in the main apparatus (FIG. 6). The flow sensor may also be present in one piece, in which case it is either integrated in the pump head or separate therefrom.

LIST OF FIGURES

FIG. 1: Front view of insulin pen (dimensions: about 120 mm×45 mm×20 mm)

FIG. 2: Rear view of insulin pen
FIG. 3: Individual components of the insulin pen
FIG. 4: Interface to the pump head
FIG. 5: Exchangeable pump head
FIG. 6: Impeller with interrupter

EXPLANATION OF REFERENCE NUMBERS

1 Insulin
2 Basic body (underside)
3 Exchangeable pump head
4 Basic body (topside)
5 Cover of cartridge compartment
6 Cartridge compartment
7 Cartridge
8 Cartridge viewing window
9 Basic body connector to receive the exchangeable pump head
10 Retainer between basic body and exchangeable pump head
11 Motor
12 Motor coupling
13 Interrupter
14 Electronics with LCD (rear side)
15 LCD display
16 Camera battery
17 Interface to PC
18 On/off switch
19 Start button
20 Dosage button
21 Contact area of the exchangeable pump head and basic body
22 Coupling to pump
23 to cartridge
24 Interface to needle
25 Needle
26 Retainer between basic body and exchangeable pump head
27 Base part of the exchangeable pump head (outerside)
28 Base part of the exchangeable pump head (outerside)
29 Cover part of exchangeable pump head
30 Rotor
31 Rolls
32 Tubing
33 Vane edge
34 Flowsensor
35 Fluid part

What is claimed is:

1. An injection device for injecting a pharmaceutical, the injection device comprising:
   a) an injection device body;
   b) a motor within the device body;
   c) a cartridge compartment within the injection device body, the cartridge compartment configured to receive a cartridge containing the pharmaceutical, the cartridge comprising a cylinder having an interior treated surface to reduce sliding forces of a movable stopper sealing one end of the cylinder and a cannula puncturable sealing disk sealing a second end of the cylinder, where the moveable stopper is configured to be slidably displaced axially towards the sealing disk within the cylinder to bring about a change in volume of the cylinder during injection;
   d) an exchangeable pump head of a peristaltic pump which is driven by the motor and by means of which the pharmaceutical is conveyed out of the cartridge; and e) control electronics comprising an adjusting mechanism, the adjusting mechanism allows presetting an amount of the pharmaceutical to be injected, the control electronics contained within the injection device body;
wherein the exchangeable pump head is configured to be detachable from and reconnectable to both the motor and the cartridge and comprises
detachable and functionally reconnectable interfaces to directly connect the exchangeable pump head to the motor and
detachable and functionally reconnectable interfaces to directly connect the exchangeable pump head to the cartridge.

2. The device as claimed in claim 1, wherein the pump head can be exchanged without employing a tool for another pump head.

3. The device as claimed in claim 1, wherein the pump head comprises a flow sensor and components of the flow sensor.

4. The device as claimed in claim 1, wherein the pump head carries a needle.

5. The device as claimed in claim 1, wherein the motor consists of a micromotor.

6. The device as claimed in claim 1, wherein the device is configured to exchangeably contain the cartridge.

7. The device as claimed in claim 1, wherein the cartridge comprises insulin.

8. A medical device for injecting a substance into a human or animal body comprising a device according to claim 1.

9. The production of a device as claimed in claim 1, where
a) a motor is provided;
b) a cartridge is provided;
c) a pump head is provided; and
d) the individual constituents as described in a) to c) are assembled to give a functional unit.

10. A medical apparatus for injecting a pharmaceutical, comprising inter alia
a) a display; and
b) a technical unit in the form of a release mechanism for starting up and carrying out the injection;
which additionally comprises at least one device as claimed in claim 1.

11. The medical apparatus as claimed in claim 10, wherein the display consists of an LCD display.

12. The medical apparatus as claimed in claim 10, which comprises
at least one means for storing and processing data and signals, and
at least one interface for transmitting data and signals to and from an external technical unit which is configured to store and process data and signals.

13. The medical apparatus as claimed in claim 10, which comprises at least one means for storing or processing data or signals, and at least one interface for transmitting data or signals to or from an external technical unit which is configured to store or process data or signals.

14. The medical apparatus as claimed in claim 13, wherein the external technical unit consists of a PC on which a program for storing or processing data or signals is installed.

15. The medical apparatus as claimed in claim 10, wherein the pharmaceutical intended for injection consists of insulin.

16. The medical apparatus as claimed in claim 15, in which the insulin is a long-acting or short-acting insulin.

17. The medical apparatus as claimed in claim 10, wherein the pharmaceutical intended for injection consists of GLP-1.

18. The medical apparatus as claimed in claim 10, wherein the pharmaceutical intended for injection consists of a heparin.

19. The production of a medical apparatus for injecting a pharmaceutical as claimed in claim 10, where at least
a) a display is provided;
b) a release mechanism is provided;
c) a device for moving liquids which comprise a pharmaceutical is provided, the device comprising a least a motor, a cartridge, a pump head which is driven by the motor and by means of which the liquid is conveyed out of the reservoir, control electronics, wherein the pump head is equipped with detachable and functionally reconnectable interfaces to the motor; and
d) at least the individual constituents as described in a) to e) are assembled to give a functional unit.

20. The production of a medical apparatus for injecting pharmaceutical as claimed in claim 19, where furthermore electronic constituents are provided and the electronic constituents being assembled with the individual constituents to give the functional unit.

21. A medical apparatus for the administration of a substance, whose pharmaceutical activity is diminished or lost in the gastrointestinal tract, for the prophylaxis or therapy of a disease or dysfunction of the body, comprising a medical apparatus according to claim 10.

22. The apparatus according to claim 21, wherein the disease is diabetes.

23. The apparatus according to claim 21, wherein the substance is insulin.

24. The apparatus according to claim 21, wherein the substance is GLP-1.

25. The apparatus according to claim 21, wherein the substance is a peptide hormone.

26. The apparatus according to claim 21, wherein the substance is a growth hormone.

27. The apparatus according to claim 21, wherein the substance is a heparin.

28. The apparatus according to claim 21, wherein the substance is Lovenox.

29. The apparatus according to claim 21, wherein the substance is a vaccine.

30. The device as claimed in claim 1, the device being a technical device.

31. The device as claimed in claim 1, wherein the pump head is furthermore equipped with detachable and functionally reconnectable interfaces to the control electronics.

32. The device as claimed in claim 1, wherein the cartridge is provided separately from the pump head, in particular in a unit comprising the motor and the control electronics.

33. The device as claimed in claim 1, wherein the pump head is removably coupled to the injection device body.

34. A device for injecting a pharmaceutical, the device comprising at least:
a housing including a motor, the housing configured to receive a cartridge comprising a cylinder having an interior treated surface to reduce sliding forces of a moveable stopper and a sealing disk, where the sealing disk is puncturable by a cannula and where the moveable stopper is configured to be displaced to bring about a change in volume of the cartridge during injection;
control electronics;
an exchangeable pump head for a peristaltic pump configured to be detachable from and reconnectable to both the housing and the control electronics,
the pump head driven by the motor and by means of which the pharmaceutical is conveyed out of the cartridge, the pump head being equipped with detachable and functionally reconnectable interfaces to the motor.

* * * * *